(12) United States Patent
Anderson

(10) Patent No.: US 8,491,569 B1
(45) Date of Patent: Jul. 23, 2013

(54) INTERMITTENT CATHETER

(75) Inventor: Robert K. Anderson, Brookshire, TX (US)

(73) Assignee: Robert K. Anderson and Eunice Anderson Family Trust, Brookshire, TX (US)

( * ) Notice: Subject to any disclaimer, the term of this patent is extended or adjusted under 35 U.S.C. 154(b) by 0 days.

(21) Appl. No.: 13/481,573

(22) Filed: May 25, 2012

Related U.S. Application Data

(60) Provisional application No. 61/574,904, filed on Aug. 11, 2011.

(51) Int. Cl.
*A61M 27/00* (2006.01)
*A61F 5/44* (2006.01)

(52) U.S. Cl.
USPC ........... 604/544; 604/327; 604/328; 604/329; 604/347; 604/349

(58) Field of Classification Search
USPC .. 604/326, 327, 544, 129, 347, 349; 606/191, 606/192
See application file for complete search history.

(56) References Cited

U.S. PATENT DOCUMENTS

| | | | |
|---|---|---|---|
| 4,696,672 A * | 9/1987 | Mochizuki et al. | 604/128 |
| 5,346,467 A * | 9/1994 | Coll | 604/8 |
| 6,840,379 B2 * | 1/2005 | Franks-Farah et al. | 206/571 |
| 7,806,888 B2 * | 10/2010 | Frassica | 604/523 |
| 2006/0271019 A1 * | 11/2006 | Stoller et al. | 604/544 |

\* cited by examiner

*Primary Examiner* — Philip R. Wiest
*Assistant Examiner* — Ariana Zimbouski
(74) *Attorney, Agent, or Firm* — Karen Bryant Tripp

(57) ABSTRACT

A catheter and method of use for bladder intermittent catheterization that helps equalize pressure between the catheter and the bladder and prevents air from traveling back into the bladder when the catheter is removed. The catheter has a distal tip that includes a reservoir which retains some urine drained from the bladder by the catheter that blocks the passage of air. Bladder spasms and pain upon removal of the catheter are avoided.

5 Claims, 3 Drawing Sheets

INTERMITTENT CATHETER

RELATED PATENT APPLICATION

This patent application claims priority from U.S. Provisional Patent Application No. 61/574,904, filed Aug. 11, 2011, and incorporates by reference that patent application in its entirety.

BACKGROUND OF THE INVENTION

1. Field of the Invention

The present invention relates to the field of catheters and more particularly to intermittent catheters used for emptying the bladder.

2. Description of Relevant Art

Intermittent catheterization is the insertion and removal of a catheter several times a day to empty the bladder. It allows regular and complete emptying of the bladder in persons unable to urinate or completely empty their bladder without help. Such persons include those with neurogenic bladders, due for example to spinal cord injury, spina bifida or multiple sclerosis, and those with non-neurogenic bladder disorders, such as may be caused for example by infravesical obstruction due to prostate enlargement, urethral strictures and post-operative urinary retention. In these persons, intermittent catheterization is used to maintain a low bladder pressure and minimal residual urine volumes in the bladder, for good bladder and renal health.

Intermittent catheterization is the preferred method of catheterization in persons who have bladder dysfunction. Even for long-term management of neurogenic bladder, intermittent self-catheterization performed by the patient or the caregiver is preferred over an indwelling urinary catheter, because intermittent catheterization has a lower risk of complications, such as infection. Nevertheless, intermittent catheterization has an early dropout rate of about 20% among children and adolescents and complications can arise. Pain or discomfort is often experienced during catheterization, especially during initiation of the catheterization and upon removal of the catheter. Methods and techniques have been proposed to ease introduction of the catheter and initiation of catheterization, but little if anything has been done to ease the pain of removal. Such pain can include bladder spasms, a burning sensation, and even bleeding.

Consequently, there is a continuing need and interest in ways to improve intermittent catheterization.

SUMMARY OF THE INVENTION

The present invention provides a product and method for intermittent catheterization of the bladder so that air does not backflow into the bladder when the catheterization is complete. That is, air does not backflow into the bladder when the catheter is removed from the bladder.

The product of the invention comprises a catheter, or a tip for positioning on the distal end of the catheter, that is, the end opposite the end that is fitted into the bladder. The catheter or catheter tip comprises a reservoir for retaining a portion of the urine drained from the bladder. In one embodiment, the reservoir may be a well in the tip for receiving and retaining some overflow of urine before the urine passes from the catheter tube into a urine disposal facility. In this embodiment, the catheter tube may be any type of tube capable of receiving the tip, and catheter tubes commonly in use are believed to be suitable.

In an alternative embodiment, the catheter or catheter tip comprises a "U" shaped loop in the tube positioned adjacent an end portion of the tube, which when in position on the main body of the catheter tube will become the distal end of the catheter tube. This end portion is folded upward and out from the catheter, such that when fitted on or part of the main body of the catheter, the "U" shaped loop appears to be at the bottom of the catheter. In this embodiment, the reservoir for receiving and retaining some overflow of urine before the urine passes from the catheter tube into a urine disposal facility is the bottom of the "U" shaped loop.

In the product of the invention, the tip comprising the reservoir may be attachable and removable from an end of the catheter tube, or may be formed as part of the catheter itself, as part of the design and shape of the catheter tube. It is contemplated that removable tips may be easily and economically added to commonly used simple, linear catheter tubes by providing the tip with a material that will slip over and/or connect to the catheter tube. An example of such a fitting is a tip comprised of a rubber or similar stretchy material that stretches over an end of the catheter tube and fits tightly around it. Another example of such a fitting is a tip comprised of the same type of material as the tube itself but only slightly larger so that tip too will fit snuggly over the end of the tube. Such tip should preferably have similar characteristics as the catheter tube if not part of the catheter tube itself, in that the tip should preferably be comprised of a material that is preferably non-allergenic, preferably does not add significantly to the weight of the catheter, and preferably is not porous to or reactive with urine or air.

The method of the invention provides a technique for intermittent catheterization of the bladder. In the method, a catheter, comprising a tube having a proximal end for insertion into the bladder and a distal end for leading the urine from the bladder into a urine disposal facility, is positioned with its proximal end in the bladder. The distal end of the catheter comprises, or has been fitted with, a reservoir for retaining a portion of the urine drained from the bladder. In the method, once the proximal end of the catheter is fitted into the bladder, urine flows into the catheter and a portion of the urine is retained in the reservoir in the distal end or tip of the catheter. When the bladder is drained of urine, the catheter is removed and the catheterization is complete. The portion of urine retained in the reservoir prevents backflow of air into the bladder when the catheter is removed and helps equalize pressure between the catheter tube and the bladder. Pain and bleeding that may result from such backflow of air is avoided.

DETAILED DESCRIPTION OF PREFERRED EMBODIMENTS

The present invention provides a catheter and method for bladder intermittent catheterization that prevents airflow back into the bladder at the completion of the catheterization so that removal of the catheter does not trigger bladder spasms, pain or bleeding. This prevention of airflow back into the bladder is effected with a reservoir in the distal catheter tip that retains some urine drained from the bladder. This reservoir also helps equalize pressure between the catheter and the bladder. Referring to the figures for illustration of the principals of the invention and to further describe the invention, FIGS. 4 and 5 show two different embodiments of the product of the invention in use, according to the method of the invention.

Figure 1:
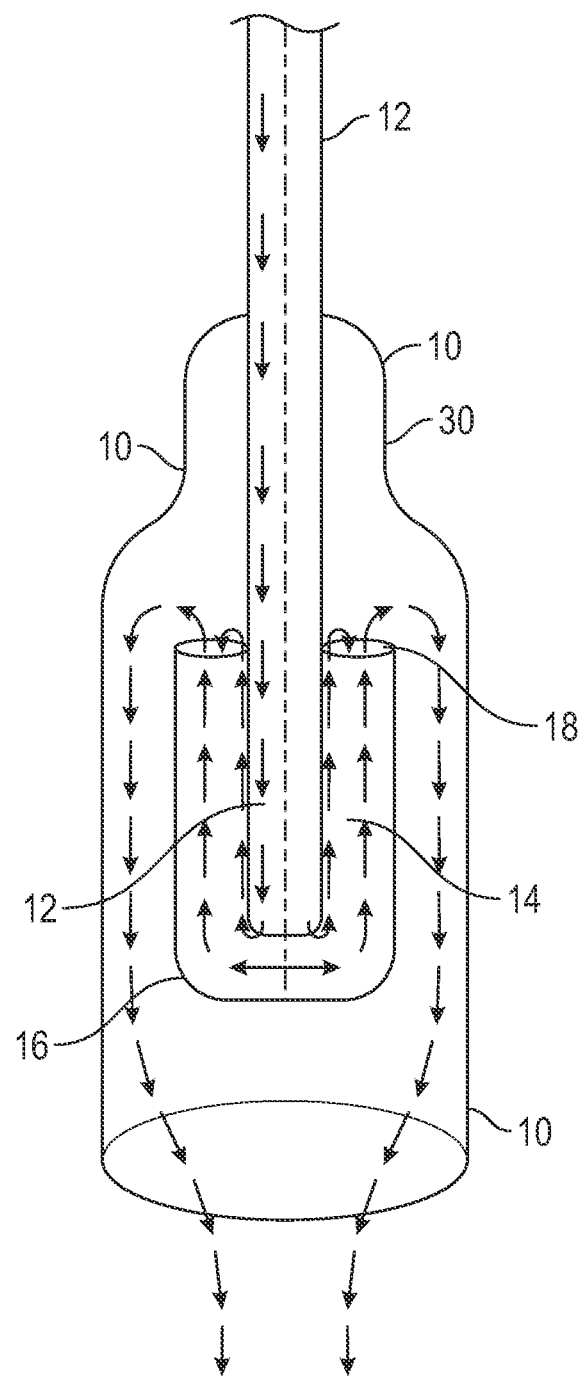
FIG. 1 is cutaway side view of one embodiment of a catheter tip of the invention, in position on the end of a catheter, showing a well comprising the reservoir for holding and retaining a portion of urine drained from the bladder by the catheter.
Figure 2:
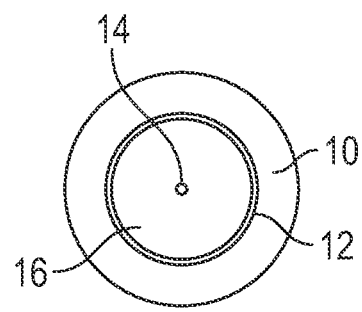
FIG. 2 is an end view of the embodiment of the catheter tip shown in FIG. 1.
Figure 5:
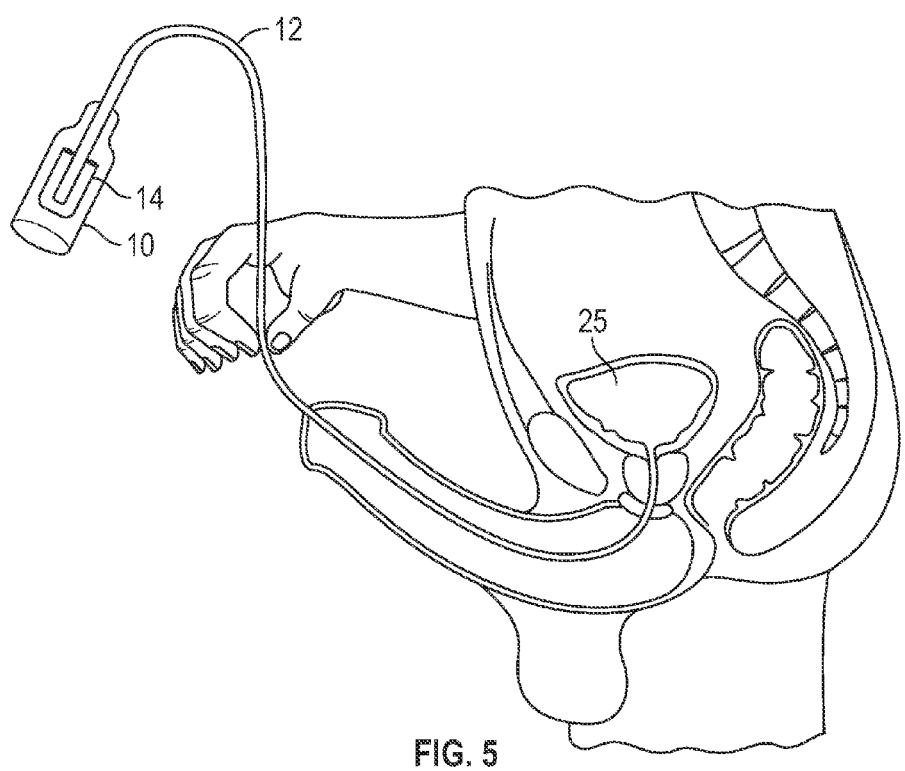
FIG. 5 is a schematic view of the embodiment of a catheter having the catheter tip shown in FIGS. 1 and 2 in use.

Referring to FIG. 1, showing the catheter of FIG. 5 in more specific detail, the catheter tip 10 of the invention is positioned on the catheter tube 12. The catheter tip in FIG. 1 is partially cut away so as to show the reservoir well 14 inside the tip 10. The reservoir well 14 has a closed bottom 16 but an open top 18 so as to receive urine from the tube 12 and cause the urine to overflow the top 18, leaving some urine behind in the well 14. FIG. 2 shows the distal end of catheter 12, showing tip 10 and more specifically the bottom of well 16 of well 14. In use, as shown in FIGS. 1 and 5, urine flows through catheter tube 12 from the bladder 25 to the distal end of the catheter tube 12 having catheter tip 10. In catheter tip 10, the urine flows into the reservoir well 14, and overflows out of the reservoir well 14, but leaving some urine behind in the reservoir well 14, and out the open end of tip 10 to a urine disposal container or facility (not shown).

Figure 3:
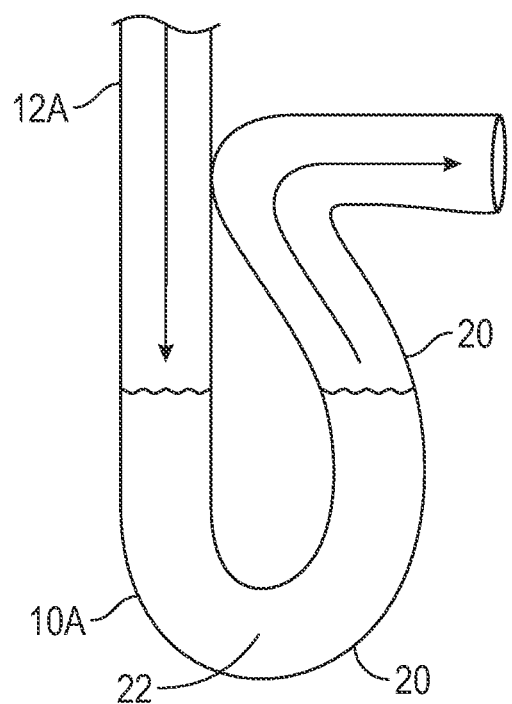
FIG. 3 is a frontal view of an alternative embodiment of a catheter tip of the invention showing a "U" shaped tube loop comprising the reservoir for holding and retaining a portion of urine drained form the bladder by the catheter.
Figure 4:
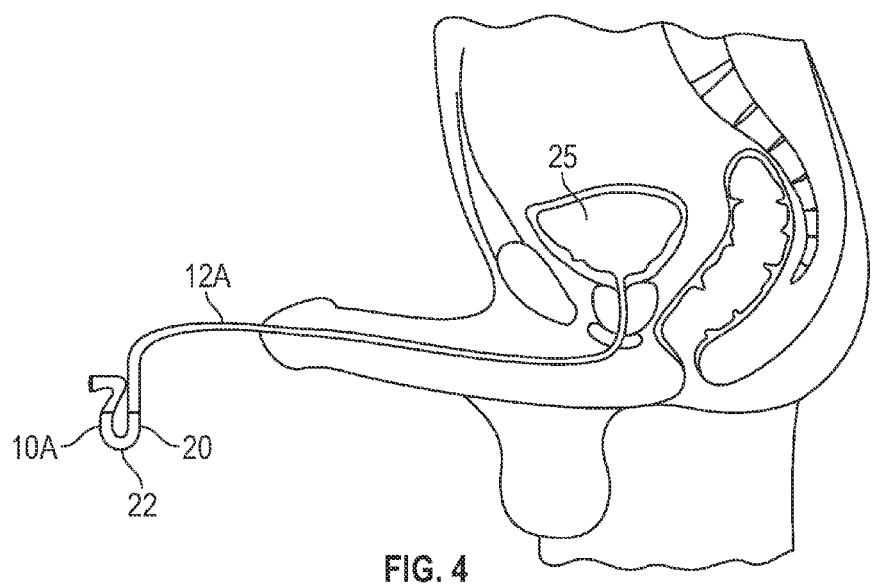
FIG. 4 is a schematic view of the embodiment of a catheter having the catheter tip shown in FIG. 3 in use.

Referring to FIG. 3, showing the catheter of FIG. 4 in more specific detail, the catheter tip 10A of the invention comprises the distal end of the catheter tube 12A. Catheter tip 10A comprises a "U" shaped loop 20 in the tube 12A. This end portion is folded upward and out from the catheter, such that when fitted on or part of the main body of the catheter, the "U" shaped loop 20 appears to be at the bottom of the catheter 12A. In this embodiment, the reservoir for receiving and retaining some overflow of urine before the urine passes from the catheter tube into a urine disposal facility is the bottom portion 22 of the "U" shaped loop 20. In use, as shown in FIGS. 3 and 4, urine flows through catheter tube 12A from the bladder 25 to the distal end of the catheter tube 12A having catheter tip 10A and down into the "U" shaped loop 20 of catheter tip 10A, leaving some urine behind in the bottom portion 22 of the loop 20, and out the open end of tip 10A to a urine disposal container or facility (not shown).

The catheter tips 10 and 10A of the invention may be formed as part of the catheter tubes 12 and 12A respectively, or may be fitted onto the distal ends of the tubes as a separate piece thereby allowing use of the present invention with already commercially available intermittent catheters. Since the catheter tips 10 and 10A of the invention are designed for the distal ends of the catheter tubes, the invention is compatible with catheters having curved, straight or tapered proximal ends and with not only unisex catheters but catheters that are gender specific to males or females or children. Further, the catheter tips 10 and 10A of the invention may be used on any length of catheter tube.

When the catheter tips are intended for fitting on existing catheters, the tips should have a connector for connecting the tip to the catheter tube, such as, for example, a connector sheath 30 as shown in FIG. 1 gripping the tube 12. This connector sheath 30 may be comprised of a gripping material such as, for example, rubber, or may be comprised of the same or similar material as the catheter tube 12 itself, such as plastic or PVC, and should preferably not be porous to or reactive with urine or air. The sheath 30 should be sized to afford a tight fit around the catheter tube 12. An alternative to a sheath 30 for connecting the tip 10 or 10A to the tube 12 or 12A respectively could be simply a slightly larger tube that fits over the distal end of tube 12. With this type of connection, tip 10A could be comprised in its entirety from this slightly larger tube and tip 10 would have a piece of such tube to fit over the distal end of tube 12 leading that end into the reservoir well 14.

The foregoing description of the invention is intended to be a description of preferred embodiments. Various changes in the details of the described catheter and method of use can be made without departing from the intended scope of this invention as defined by the appended claims.

I claim:

1. An intermittent catheter for intermittent catheterization of the bladder, comprising:
    a tube for receiving urine from the bladder, the tube having a proximal end for insertion into the bladder and a distal end for draining the urine away from the bladder; and
    an overflow reservoir comprising a preformed well within the distal end of the tube for receiving urine and for retaining a portion of the urine so as to prevent backflow of air into the bladder when the tube is removed from the bladder to complete the intermittent catheterization;
    wherein the reservoir allows urine not retained in the well to pass into a disposal receptacle during the intermittent catheterization; and
    wherein the overflow reservoir comprises a preformed "U" shaped loop such that the well is the bottom portion of the "U".

2. A tip for placement or insertion on the distal end of an intermittent catheter tube for bladder intermittent catheterization, the tip comprising an overflow reservoir having a preformed well for receiving and retaining a portion of urine from the bladder during intermittent catheterization, so as to prevent backflow of air into the bladder when removing the tube to complete intermittent catheterization, while allowing the remainder of the urine to pass into a disposal receptacle during intermittent catheterization, wherein the reservoir comprises a preformed "U" shaped loop and the bottom of the "U" shaped loop is the well.

3. The tip of claim 2 wherein the reservoir further comprises a preformed bent or folded end portion such that when fitted onto the catheter the folded end portion appears to be folded upward and out with respect to the catheter and the "U" shaped loop appears to be at the bottom of the catheter.

4. A method for intermittent catheterization of the bladder comprising:
    beginning intermittent catheterization by inserting into the bladder an intermittent catheter for receiving urine from the bladder wherein the catheter comprises a tube having a proximal end for insertion into the bladder and receiving urine and a distal end for allowing the urine to flow out of the tube into a disposal receptacle, wherein the tube comprises an overflow reservoir having a preformed well for receiving and retaining a portion of the urine passing through the distal end of the tube so as to prevent backflow of air into the bladder when the intermittent catheterization is complete, and wherein the overflow reservoir comprises a preformed "U" shaped loop and the bottom of the "U" shaped loop is the well;
    allowing flow of urine from the bladder into the catheter tube;

collecting and retaining a portion of the urine in the reservoir well;

allowing the remainder of the urine to flow out of the tube into a disposal receptacle; and thereafter removing the catheter to complete the intermittent catheterization without any backflow of air into the bladder.

5. The method of claim 4 wherein the "U" shaped loop comprises the tip of the distal end of the tube which is bent or folded upward and out such that backflow of air through the tube into the bladder is prevented.

* * * * *